(12) United States Patent
Frank et al.

(10) Patent No.: US 10,081,503 B2
(45) Date of Patent: *Sep. 25, 2018

(54) REAGENT STORE

(71) Applicant: Roche Molecular Systems, Inc., Pleasanton, CA (US)

(72) Inventors: Paul Frank, Ennetbuergen (CH); Andreas Gisler, Thalwil (CH); Robert Huesler, Root (CH); Rolf Knobel, Rotkreuz (CH); Markus Rinderknecht, Adligenswil (CH)

(73) Assignee: Roche Molecular Systems, Inc., Pleasanton, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/733,543

(22) Filed: Jun. 8, 2015

(65) Prior Publication Data

US 2015/0266679 A1 Sep. 24, 2015

Related U.S. Application Data

(63) Continuation of application No. 13/297,853, filed on Nov. 16, 2011, now Pat. No. 9,080,998.

(30) Foreign Application Priority Data

Nov. 22, 2010 (EP) .................................. 10192034

(51) Int. Cl.
| | |
|---|---|
| *G01N 35/10* | (2006.01) |
| *G01N 35/00* | (2006.01) |
| *B65G 65/00* | (2006.01) |
| *B65G 47/74* | (2006.01) |

(52) U.S. Cl.
CPC ........... *B65G 65/005* (2013.01); *B65G 47/74* (2013.01); *G01N 35/00732* (2013.01); *G01N 35/00871* (2013.01); *G01N 35/10* (2013.01); *G01N 35/1002* (2013.01); *B65G 2201/0235* (2013.01); *B65G 2203/0216* (2013.01); *B65G 2814/0302* (2013.01); *G01N 2035/00435* (2013.01); *G01N 2035/00673* (2013.01); *G01N 2035/00772* (2013.01); *G01N 2035/00811* (2013.01); *G01N 2035/1051* (2013.01)

(58) Field of Classification Search
None
See application file for complete search history.

(56) References Cited

U.S. PATENT DOCUMENTS

| | | | |
|---|---|---|---|
| 7,182,912 B2 | 2/2007 | Carey et al. | |
| 7,381,370 B2 | 6/2008 | Chow et al. | |
| 2003/0202905 A1 | 10/2003 | Devlin, Sr. et al. | |
| 2005/0013735 A1 | 1/2005 | Gebrian et al. | |
| 2007/0255756 A1* | 11/2007 | Satomura | G01N 35/00663 |

(Continued)

FOREIGN PATENT DOCUMENTS

| | | |
|---|---|---|
| EP | 1959257 A2 | 8/2008 |
| EP | 1959257 A3 | 11/2008 |

(Continued)

*Primary Examiner* — Patricia Kathryn Wright
(74) *Attorney, Agent, or Firm* — Pamela C. Ancona; David J. Chang

(57) ABSTRACT

An automated analyzer with an on-board fridge for long-term cooling of reagents, and a method for isolating and analyzing an analyte comprising long-term cooling of reagents.

5 Claims, 13 Drawing Sheets

(56) References Cited

U.S. PATENT DOCUMENTS

| | | |
|---|---|---|
| 2009/0003981 A1 | 1/2009 | Miller |
| 2009/0035867 A1 | 2/2009 | Yagi et al. |
| 2009/0117620 A1 | 5/2009 | Fritchie et al. |
| 2009/0129979 A1 | 5/2009 | Kegelman et al. |
| 2010/0132484 A1 | 6/2010 | Schacher et al. |
| 2011/0269239 A1* | 11/2011 | Diessel ............... G01N 35/028 436/43 |

FOREIGN PATENT DOCUMENTS

| | | |
|---|---|---|
| EP | 1498734 B1 | 5/2009 |
| WO | 199302348 A1 | 2/1992 |

* cited by examiner

REAGENT STORE

CROSS-REFERENCES TO RELATED APPLICATIONS

The present application is a continuation of U.S. patent application Ser. No. 13/297,853, filed on Nov. 16, 2011, which claims the benefit of priority under 35 U.S.C. § 119 of EP10192034.6, filed Nov. 22, 2010, the contents of which are incorporated by reference herein in their entireties.

FIELD OF THE INVENTION

The present invention relates to an automated analyzer and an automated system for detecting or quantitating analytes and a method for detecting or quantitating an analyte in a sample.

BACKGROUND OF THE INVENTION

Automated analyzers are commonly used diagnosing conditions in individuals, or for testing pools of samples from one or multiple individuals. For analyzing an analyte in a sample, reagents are required. Such reagents have to be provided to the analyzer and distributed within the analyzer. Therefore, reagents are commonly kept in reagent cassettes which can be loaded or unloaded into or from the analyzer. Frequently, such reagents are temperature sensitive. In some analyzers, reagents are only loaded for a single load and then manually retrieved and transferred into a refrigerator. Analyzers are also known with onboard cooled storage.

The present invention provides for improved automated analyzers, systems and methods comprising cooled storage of reagents.

SUMMARY OF THE INVENTION

The present invention relates to an automated analyzer for isolating and/or analyzing an analyte. The analyzer of the present invention comprises a unit for transferring a liquid. This unit comprises a station for presenting a reagent cassette to a pipetting device. The analyzer further comprises a unit for isolating said analyte. Furthermore, the analyzer comprises a closed reagent store for storing reagents. Such reagents preferably comprise reagents necessary for performing the analysis. The closed reagent store comprises a cooling unit for active cooling. Furthermore, it comprises an internal storage and retrieval unit. In order to allow input and output of reagent cassettes, a closure is comprised in the closed reagent store. The closed reagent store also comprises an identification unit for identifying the contents of a reagent cassette. For automated transport of the reagent cassettes between the closed reagent store to other stations of the analyzer and back to the reagent store, the analyzer also comprises a handler system for bidirectional transport of said reagent cassette between said reagent store and said station for presenting a reagent cassette.

The present invention also relates to a method for providing reagents to an analytical system comprising the steps of:
loading reagent cassettes into a reagent store;
identifying said cassettes;
automatically transferring said cassettes into said reagent store;
positioning said cassettes within said reagent store;
transferring instructions from a control unit to said reagent store, wherein said instructions specify which cassettes are required by the system;
providing said cassettes to a handler system;
transporting said cassettes with said handler system to a station for presenting said cassettes to the system;
returning said cassette to said reagent store or transferring said cassette to a waste station.

DETAILED DESCRIPTION OF THE INVENTION

Figure 1A:
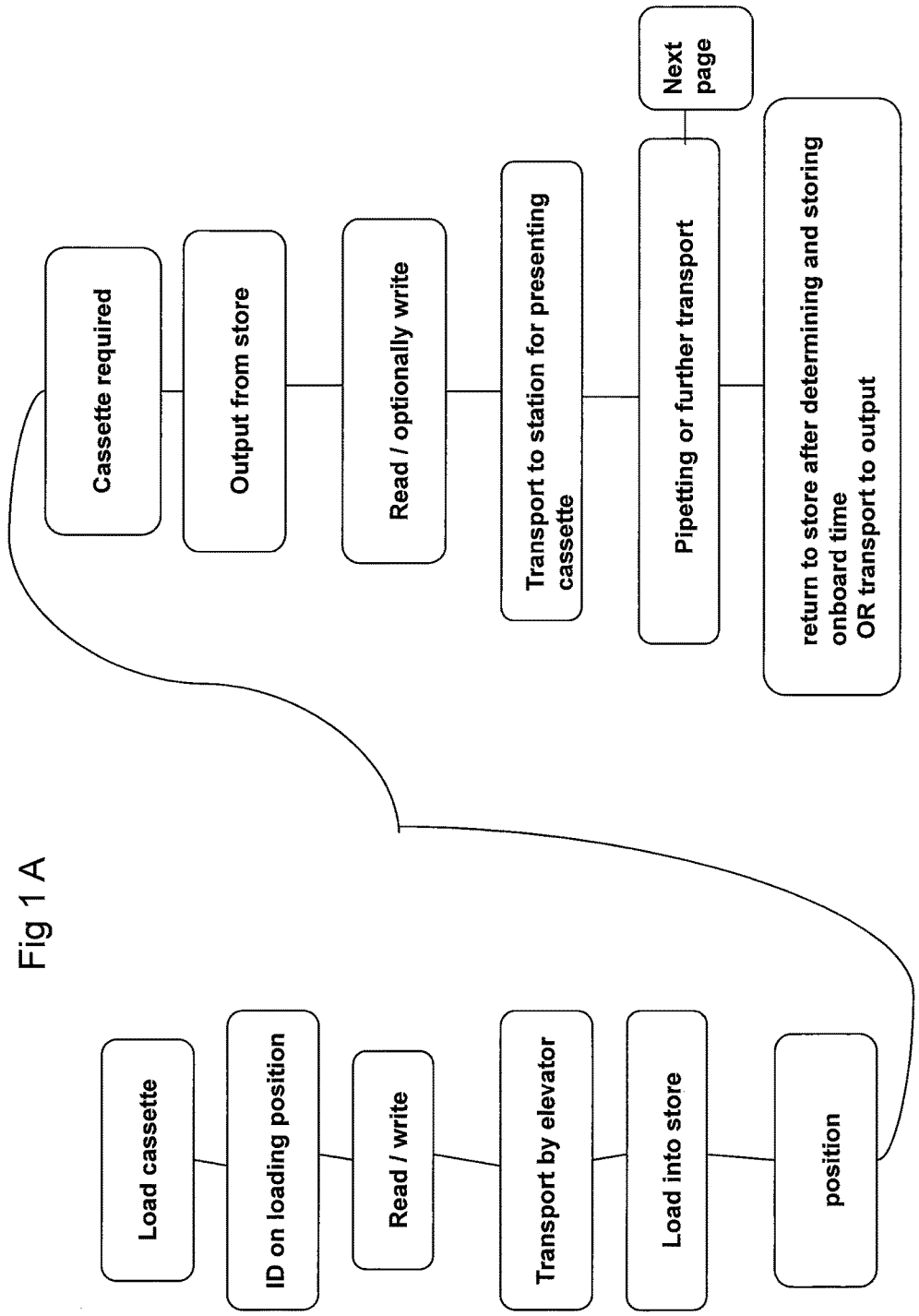
FIG. 1A shows a workflow of reagent cassettes in analyzer comprising reagent stores.

The Reagent Store
The present invention relates to an automated analyzer for isolating and/or analyzing an analyte.

The terms "analytical apparatus"(400) and "analyzer" (400) and "analytical instrument" (400) are used interchangeably. An analytical system comprises an analyzer. An analyzer comprises one or more modules or cells or units. Said modules or cells or units comprise stations for carrying out the processing and/or analysis of an analyte.

The term "analyte" as used herein may be any type of biomolecule which is of interest for detection, and the detection thereof is indicative of a diagnostic status of an organism. The organism can be animal or, in one embodiment, human. Analytes may be proteins, polypeptides, antibodies or nucleic acids. In one embodiment, the analyte is a nucleic acid. The analyte may be present in a liquid sample, or it may be present as a solid sample affixed to a support. Solid samples may include tissue.

The term "detecting" as used herein relates to qualitative measurement of an analyte.

The analyzer of the present invention comprises a unit for transferring a liquid.

The term "liquid" as used herein relates to any type of liquid which has to be transferred during an analytical process. Thus, the term includes liquid samples. It also includes reagents or suspensions of reagents.

The unit for transferring liquids comprises a station for presenting a reagent cassette to a pipetting device. In one embodiment, said unit is a unit or cell or module in which reagents are transferred from said reagent cassette to at least one receptacle. In one embodiment, said unit comprises a pipetting device for transferring samples from a sample vessel to at least one receptacle, and for transferring control reagents to said at least one receptacle. Embodiments of pipetting devices, reagent cassettes, receptacles and control reagents are further described herein. In one embodiment, said unit for transferring liquids is a unit for preparing a reaction mixture. In such a unit, reagents are added to an analyte prior to reaction. A reagent cassette can refer to a container comprising a liquid or suspension of reagents. Or a reagent cassette can be a holder for holding containers comprising a liquid or a suspension of reagents.

In one embodiment, the analyzer further comprises a unit for isolating said analyte. Said unit for isolating said analyte and said unit for transferring liquids may be located on a processing deck, and said closed reagent store may located below said processing deck. This has the advantage that space can be saved and the footprint of the analyzer can be significantly reduced. One embodiment is also comprised wherein the unit for transferring liquids and the unit for isolating said analyte are merged into one unit.

In a further embodiment, the analyzer additionally comprises a unit for reacting said analyte to obtain a detectable signal. In an embodiment, said unit for reacting said analyte to obtain a detectable signal also comprises a detection unit. In another embodiment, said analyzer additionally comprises a separate detection unit.

The term "processing deck" as used herein relates to a deck on which samples are processed. The processing deck may be one deck on which all stations necessary for processing are located. In a system comprising more than one module, the term "processing deck" includes all the decks within the different modules which comprise stations for processing a sample. Thus, the term "processing deck" may also include the different decks in different modules of an analyzer.

In another embodiment, said unit for transferring liquids comprises a separation station for isolating and purifying an analyte. In one embodiment, the station for presenting a reagent cassette to a pipetting device is also disposed on said processing deck. In one embodiment, the closed reagent store is disposed at a lower level, most preferably below said processing deck. Thus, in one embodiment, the closed reagent store and the station for presenting a reagent cassette to a pipetting device are separate. One advantage is that the space of the analyzer can be used in an optimal way by also using space underneath the processing deck.

Furthermore, the analyzer comprises a closed reagent store for storing reagent cassettes. A closed reagent store is understood to relate to an incubator with a casing, wherein said casing is insulated from the environment and comprises a closure which allows opening and closing the incubator to add or retrieve reagent cassettes. Embodiments of closures are doors or shutters or, in one embodiment, a drawer. Said reagent store may additionally be suitable for storing other containers comprising reagents.

Reagents comprise reagents necessary for performing the analysis. Reagents necessary for performing the analysis of analytes include reagents for sample preparation, control reagents, reagents for reacting with the analyte to obtain a detectable signal, and/or reagents necessary for detecting the analyte. Such reagents may include reagents for isolating an analyte and/or reagents for processing a sample and/or reagents for reacting with an analyte to obtain a detectable signal and/or washing reagents and/or diluents.

The closed reagent store comprises a cooling unit for active cooling. The term "active cooling" is understood to mean that the incubator is kept within a predefined range of temperatures. A range of temperatures is between $-4°$ C., or $-2°$ or $0°$ C. or $2°$ C. to $10°$ C., or $8°$ C. or $6°$ C. or $4°$ C.

Furthermore, it comprises an internal storage and retrieval unit. The internal storage and retrieval system comprises a transport mechanism, in one embodiment an elevator, for transporting a reagent cassette into the reagent store, and storage positions, at least one turntable which, in one embodiment comprises centering blocks for positioning reagent cassettes. This allows for efficient internal storage and retrieval. In one embodiment, the elevator comprises a Y-handler.

In order to allow input and output of reagent cassettes, a closure is comprised in the closed reagent store.

The closed reagent store also comprises an identification unit for identifying the contents of a reagent cassette.

For automated transport of the reagent cassettes between the closed reagent store to other stations of the analyzer and back to the reagent store, the analyzer also comprises a transport system for bidirectional transport of said reagent cassette between said reagent store and said station for presenting a reagent cassette. Said system for bidirectional transport may comprise conveyors. In one embodiment, said transport system comprises at least one handler. In one embodiment, said handler system comprises at least two, or at least three handlers. One advantage of a handler system is that the closed reagent store can be located underneath the processing deck.

Handlers and pipetting devices are well known in the art.

In one embodiment of the analyzer described herein, the analyzer comprises a control unit for transferring instructions to said closed reagent store, wherein said instructions specify the reagent cassette required by the system. Such control units may comprise processors and are known to the skilled person.

In one embodiment, the store and a temporary store are comprised on the same module of an analyzer. In another embodiment, they are comprised on different modules of an analyzer. In one embodiment, the analyzer is a self-contained analyzer with comprising stations within an open space devoid of any spatial separation.

The present invention also relates to a method of providing reagents to an analytical system comprising the steps of:
  loading reagent cassettes onto a loading interface of a reagent store;
  identifying said reagent cassettes;
  transferring said reagent cassettes into said reagent store;
  positioning said reagent cassettes within said reagent store;
  transferring instructions from a control unit to said reagent store, wherein said instructions specify which reagent cassettes are required by the system;
  providing a reagent cassette to a transport system;
  transporting said reagent cassette with said transport system to a station for presenting said reagent cassette to a pipetting device;
  returning said reagent cassette to said reagent store or transferring said reagent cassette to a waste station.

This method allows for returning partly used reagent cassettes to the cooled reagent store until further use. The life time of the reagents can, thus, be prolonged, and reagents in a cassette can be used until the cassette is empty.

A loading interface is an interface associated with the closure herein described which receives the reagent cassettes loaded by the operator, a preferred embodiment is the drawer herein described. In one embodiment, the operator manually loads the reagent cassettes into the drawer of the closed reagent store. The drawer then automatically closes. The reagent cassettes are identified. In one embodiment, all steps after loading and before retrieval of reagent cassettes are automated.

In one embodiment of the method described herein, the reagent store is a closed reagent store as described herein. Thus, said closed reagent store is preferably cooled by an active cooling unit. In one embodiment, said positioning of said cassettes within said store and said providing of said cassettes is performed by an internal storage and retrieval unit.

In one embodiment of the method herein described, said reagent cassettes comprise at least one tag for reading and writing information. In one embodiment, said method comprises storing onboard time on said tag. In one embodiment, said storing of onboard time on said tag is done when providing said cassettes from said store to said handler system. In one embodiment, said storing of onboard time comprises writing of a time stamp on said tag. Thus, in one embodiment, the method additionally comprises determining and storing onboard time. Said determining and storing onboard time is triggered when providing said reagent cassette from said store to said transport system. Said storing of onboard time may be done with a decremental counter before returning said reagent cassette to said reagent store. Further embodiments are described herein.

Thus, in one embodiment, said storing of onboard time comprises storing of onboard time with a counter. The counter may be a decrementing counter. The speed of the decrementing counter is increased with increased temperature. Thus, the speed of the decrementing counter is related, or is proportional to the difference between the temperature of the area of the presence of the reagent cassette and the reagent store for long term storage. For the embodiment of the onboard time stamp, said time stamp is then compared with the actual time, an on-board time is calculated based on said time stamp and the actual time, and a cumulated onboard time is calculated and written on said tag before returning said cassette to said reagent store.

It is understood that whenever a process step is described herein which relates to writing an onboard time stamp to track onboard time, the same process step can be replaced with determining onboard time using a counter, in one embodiment a decremental counter. An incremental counter is an alternative for counting onboard time. The lifetime of the reagents can, thus, be monitored and reagent use can be optimized.

The term "actual time" is understood to be the time when the respective process step is carried out.

Once reagents are presented to a pipetting device, said reagents are transferred from said reagent cassette held in said station for presenting said reagent cassette to at least one receptacle by a pipetting device.

Figure 1B:
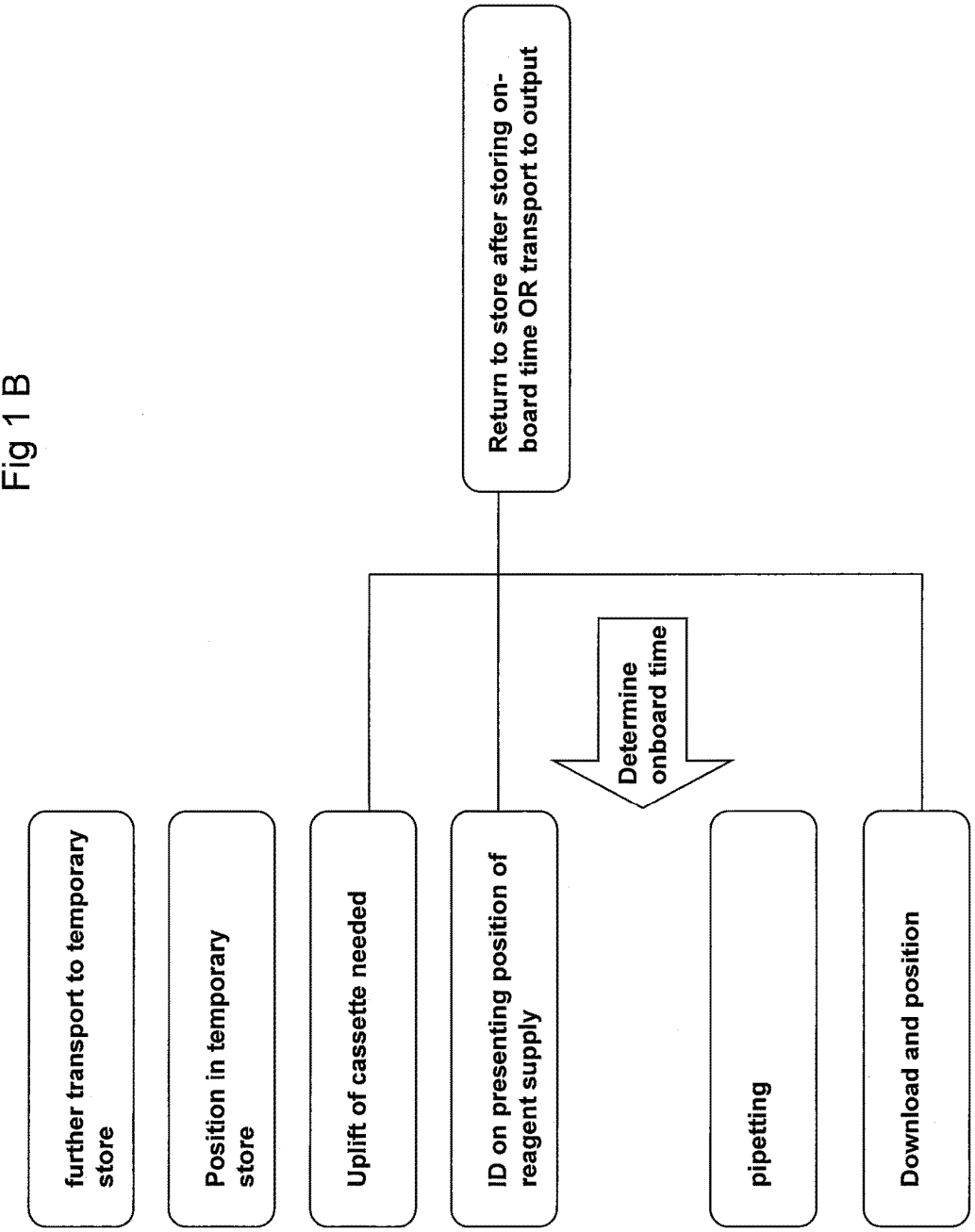
FIG. 1B shows the workflow for further transport.

One embodiment of a workflow for the method herein described is described in more detail in FIG. 1. Reagent cassettes comprise a tag for storing information. Said information comprises information about on-board time, in one embodiment, on-board time in different temperature compartments. The tag is an RFID tag. Reagent cassettes are loaded onto the analyzer and stored in the reagent store described herein. A loading flag is written onto the tag upon loading to store the loading date. The control system stores information on the type of reagent or reagents stored in a reagent cassette and the location of the reagent cassette within the store. Upon receipt of information regarding reagents which are required by the analytical system, the handler system retrieves and transports the required cassette or cassettes to a station for presenting a reagent cassette to the analyzer. A counter on the tag is now triggered to decrementally count during time spent outside the reagent store. Alternatively, an onboard time stamp may be written onto the tag. The reagent cassette is now transported either to a station for presenting a reagent cassette to a pipetting device or to the temporary reagent store herein described. If the reagent cassette is transported to a station for presenting a reagent cassette to a pipetting device, the reagent cassette is either returned to the reagent store after use, or is transferred to a waste station. If the reagent cassette is transferred back to the reagent store, an onboard time stamp may be written on the tag. The process may then be repeated.

If the reagent cassette is transported to the temporary store, an onboard time stamp may be written onto the tag before placing the reagent cassette in the temporary store, if a time stamp is used to monitor on-board time. With the counter, the decremental counting occurs according to the temperature in the temporary store. The location of the cassette in the temporary store is stored by the control system. If the system requires reagents, the corresponding reagent cassette is transferred to a station for presenting a reagent cassette to a pipetting device. The advantage of the temporary store is that a reagent cassette can be presented to the pipetting device very quickly. While the reagent cassette is located on the station for presenting a reagent cassette, the counter counts faster than in the temporary store if the temperature on the station for presenting a reagent cassette is higher than in the temporary store. The reagent cassette may be returned to the temporary store for re-use or to the reagent store for long time storage. An on-board time stamp is written onto the tag prior to storage in the reagent store. An onboard time counter is updated. The reagent cassette is then stored in the reagent store until it is required again.

If total onboard time exceeds a preset value, if reagent levels in the reagent cassette are too low or if the reagent cassette is erroneous, it is transported to a waste station or to an input/output position for manual removal.

Figure 11:
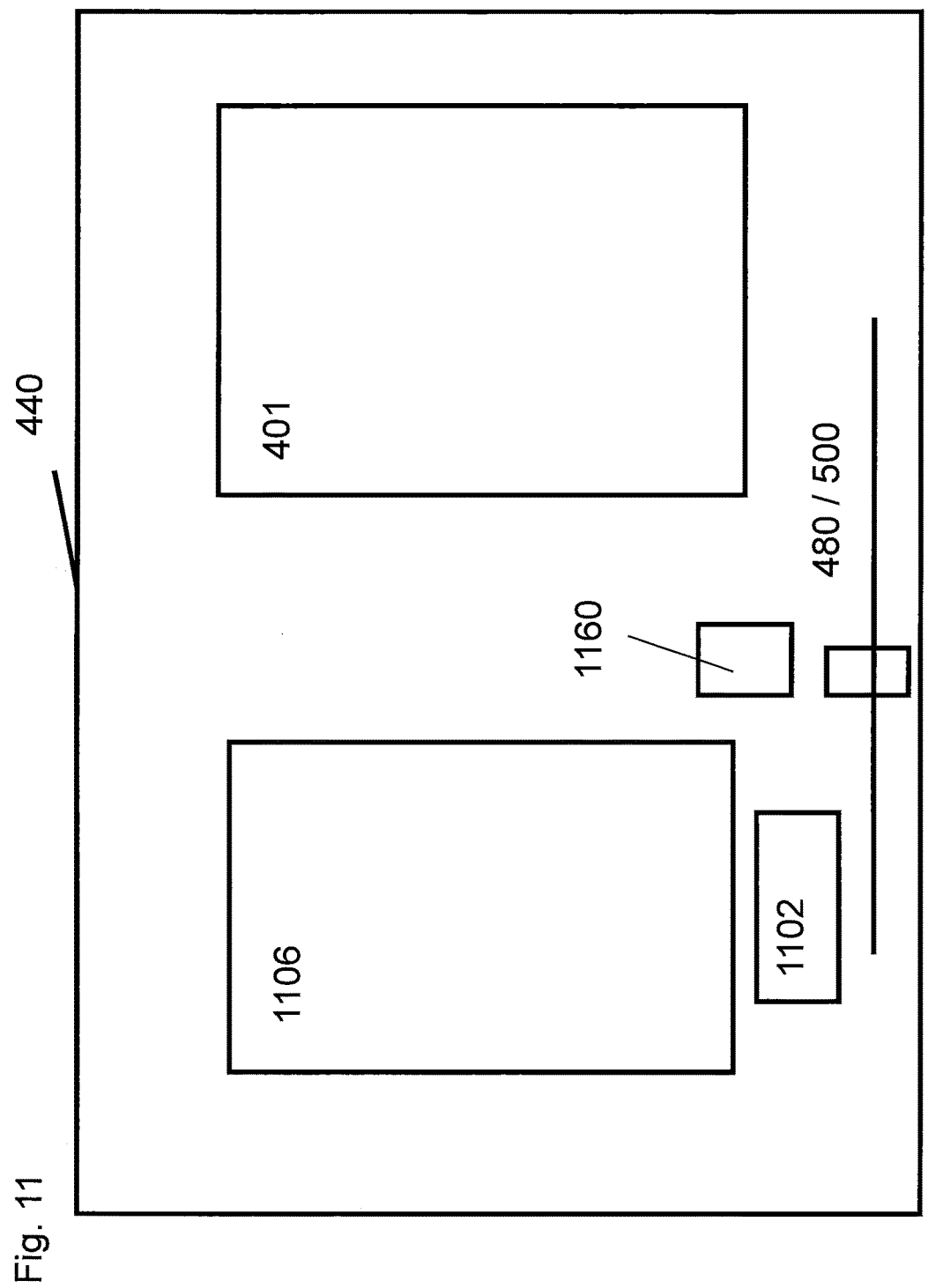
FIG. 11 shows a second schematic view of analytical system.

The analytical system herein described, thus, comprises a reading/writing device (1160) (as shown in FIG. 11).

Also within the scope of the present invention are analyzers and systems for isolating and/or analyzing an analyte as described herein, which comprise a reagent store as described herein.

Furthermore, a method for analyzing an analyte in a system comprising a reagent store as described herein is also within the scope of the present invention.

A method for isolating and analyzing an analyte that may be present in a liquid sample is disclosed. Said method comprises the automated steps of
  a) transferring said liquid sample from a sample vessel to a processing vessel with a pipette tip;
  b) combining together a solid support material and said liquid sample in a well of said processing vessel for a period of time and under conditions sufficient to permit said analyte to be immobilized on the solid support material;
  c) isolating the solid support material from other material present in the liquid sample in a separation station;
  d) and purifying the analyte in the separation station by separating the liquid sample from the solid support material and washing the materials one or more times with a wash buffer.

In one embodiment, the processing vessel may comprise more than one receptacle. In one embodiment, the processing vessel is a multiwell plate. The method, in one embodiment, additionally comprises the step of e) reacting said purified analyte with reagents necessary to obtain a detectable signal.

The term "receptacle" as used herein relates to a single vessel (or tube) or to a tube comprised in a multi-tube unit, or to a well (or vessel) of a multiwell plate.

The term "vessel" is understood to mean a single vessel or a single vessel in a multi-tube unit, a multiwell plate or a multi-tube unit or a well of a multiwell plate.

In one embodiment, the reacting comprises generating a detectable signal. Furthermore, the method may additionally comprise the step of detecting a detectable signal.

The term "reacting" as used herein relates to any type of chemical reaction of the analyte with reagents that is necessary to obtain a detectable signal. In one embodiment, said reacting comprises amplification. Amplification may be understood as any type of enhancement of a signal. Thus, amplification can be a conversion of a molecule by an enzyme, wherein said enzyme is coupled or bound to the analyte, leading to a detectable signal, wherein more signal molecules are formed than analyte molecules are present. One such non-limiting example is a formation of a chemiluminescent dye, e.g. using ECL. The term amplification further relates to nucleic acid amplification, if the analyte is a nucleic acid. This includes both linear, isothermal and exponential amplifications. Non-limiting examples of nucleic acid amplification methods are TMA, SDA, NASBA, PCR, including real-time PCR. Such methods are well known to the skilled person.

The term "solid support" as used herein relates to any type of solid support to which the analyte is capable of binding, either directly and non-specifically by adsorption, or indirectly and specifically. Indirect binding may be binding of an analyte to an antibody immobilized on the solid support, or binding of a tag to a tag binding compound, e.g. binding of 6xHis tags to Ni-chelate. When the analyte is a nucleic acid, such indirect binding may be by binding to a capture nucleic acid probe which is homologuous to a target sequence of the nucleic acid of interest. Thus, using capture probes attached on a solid support, a target analyte, or a target nucleic acid, can be separated from non-target material, or non-target nucleic acid. Such a capture probe is immobilized on the solid support. Solid support material may be a polymer, or a composition of polymers. Other types of solid support material include magnetic silica particles, metal particles etc.

Non-specific binding of nucleic acid to silica particles occurs in the presence of chaotropic compounds. Such binding may also be referred to as direct binding, as opposed to the indirect binding described herein. In one embodiment, the solid supports silica particles which comprise a magnetic or magnetizable material.

Figure 2:
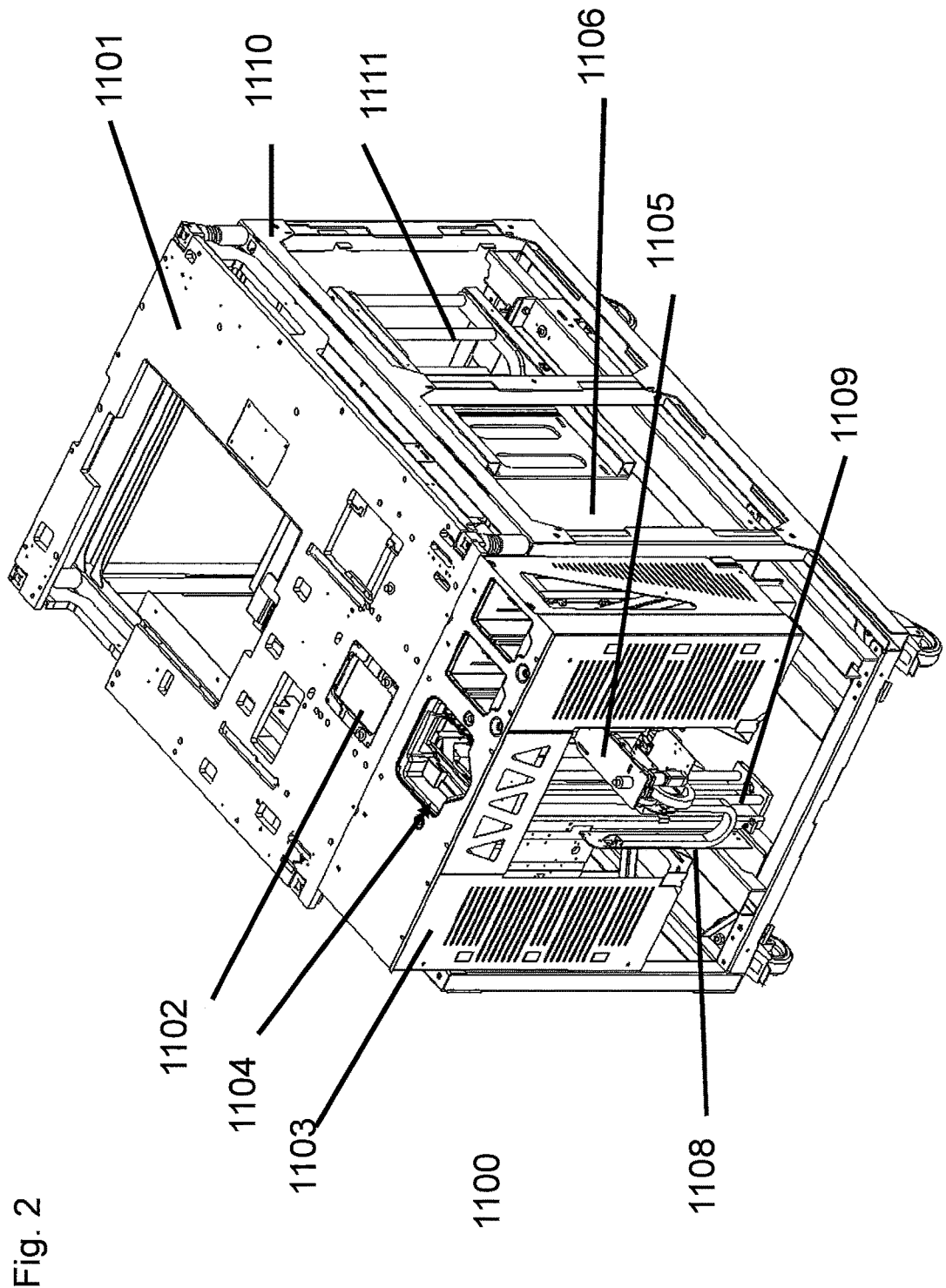
FIG. 2 shows a view of lower part of analyzer module with stacker and reagent store.
Figure 3:
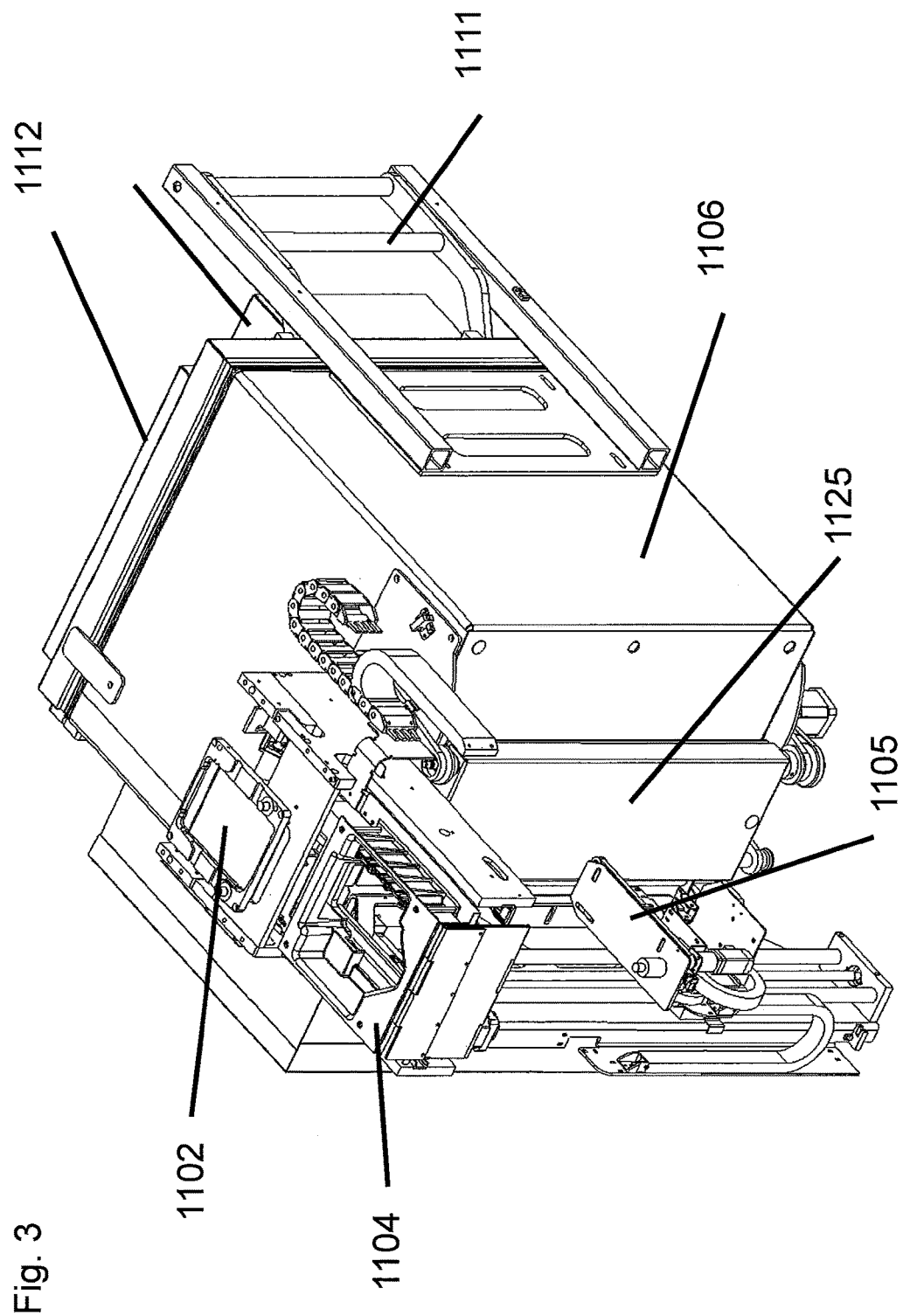
FIG. 3 shows a closed reagent store.

FIG. 2 shows the lower part (1100) of a module of an analyzer. On top is a processing plate (1101). Lower part (1100) comprises a frame (1110). The processing plate comprises a station (1102) for presenting a reagent cassette (1122). The housing of a stacker unit is also shown (1103). The stacker unit further comprises a reagent drawer (1104) into which reagent cassettes are loaded. An elevator (1105) then moves the cassette to a level where it can be transferred into the reagent store (1106). The elevator comprises a Y handler (1105) and a Z-axis (1108). The spindle (1109) of the elevator (1105) is also shown. Also visible is an arrangement (1111) for opening a back door of the store (1106). The store (1106) and the back door (1112) as well as the cooling unit (1115) is shown in FIG. 3.

Figure 4:
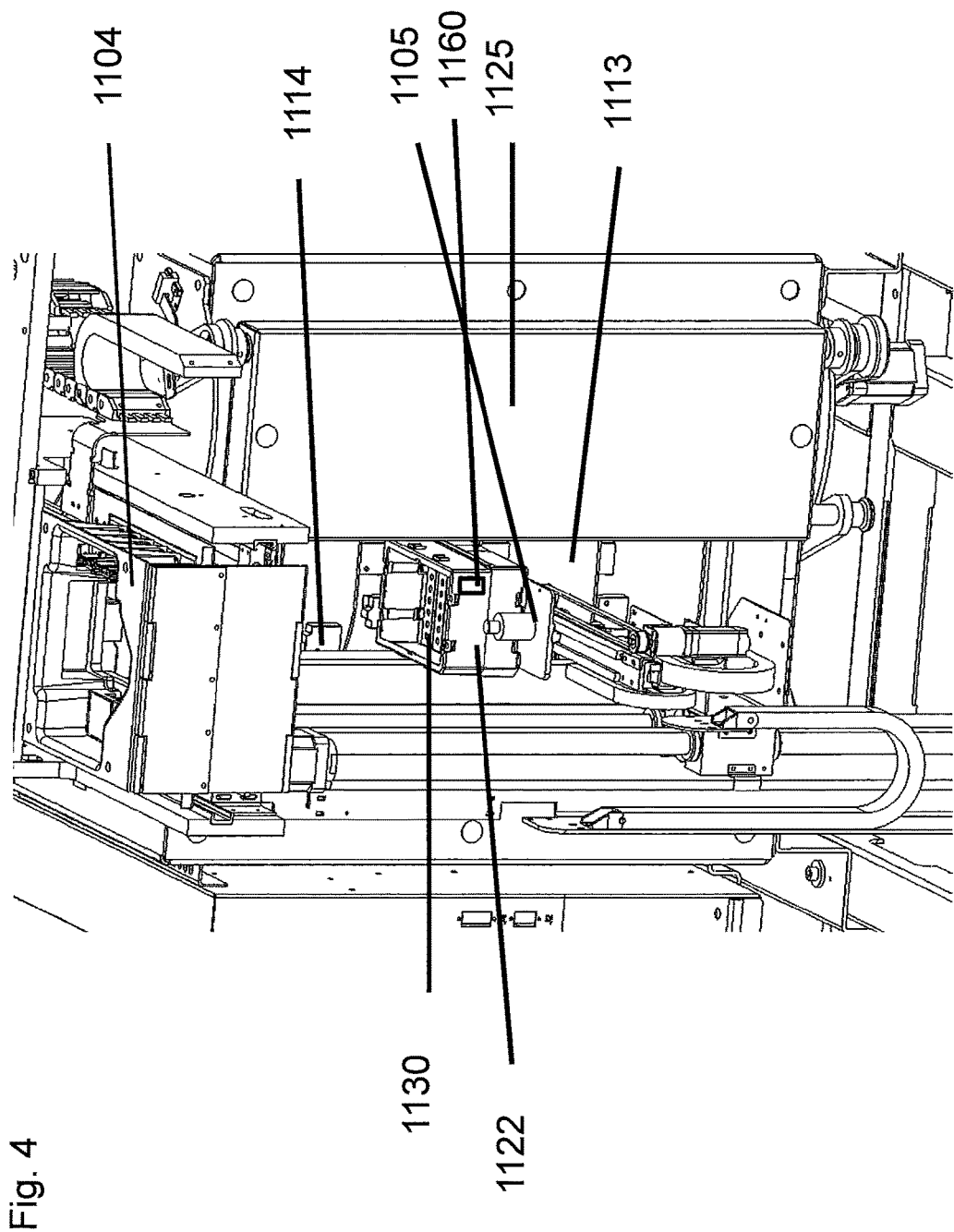
FIG. 4 shows a view of loading of reagent cassette into reagent store.

FIG. 4 shows the reagent cassette drawer (1104), the open front door (1125) of the reagent store (1106) and a reagent cassette (1122) comprising reagent inserts (1130). The reagent cassette (1122) is positioned on the Y handler (1105). The Y handler (1105) is about to place the reagent cassette (1102) into the store (1106). The interior of the store (1106) comprises turn tables (1113) on which reagent cassettes (1122) are placed and can be positioned. The turn tables (1113) comprise centering blocks (1114) in which the cassettes (1122) are positioned. A preferred number of centering blocks (1114) is 4 blocks (1114).

Figure 12:
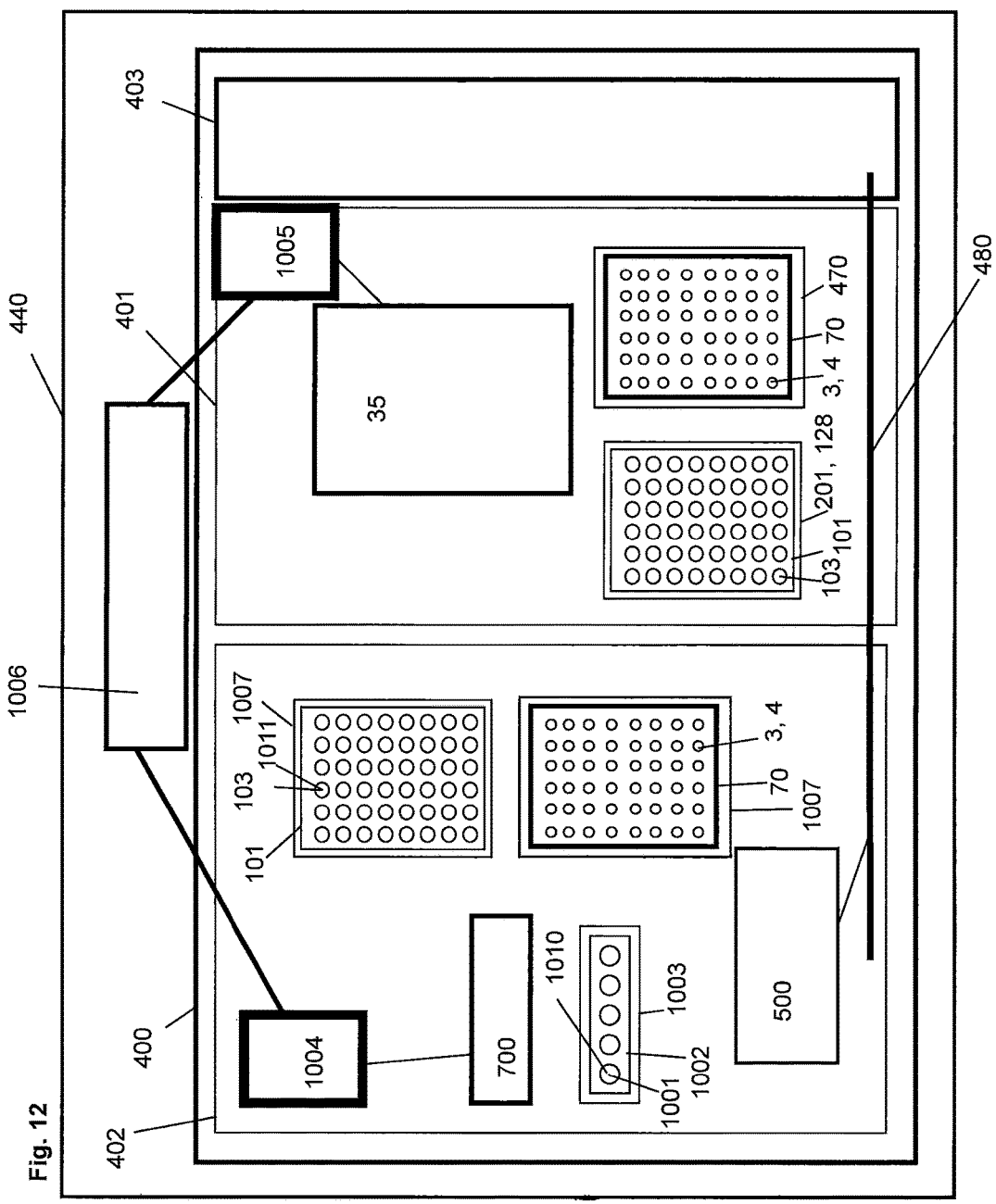
FIG. 12 shows a third schematic view of analytical system.

An automated analyzer (400) for use in performing a nucleic acid based amplification reaction is shown in FIG. 12. Said analyzer comprises a plurality of modules (401, 402, 403). One module is a processing module disposed at a first location within the analyzer constructed and arranged to separate a nucleic acid from other material in a sample. Said processing module comprises a separation device as herein described. The analyzer further comprises an amplification module disposed and arranged at a second location within the analyzer. The amplification module comprises a temperature-controlled incubator for incubating the contents of at least one receptacle, preferably of a multiwell plate comprising the separated nucleic acid and one or more amplification reagents for producing an amplification product indicative of the target nucleic acid in the sample.

Figure 10:
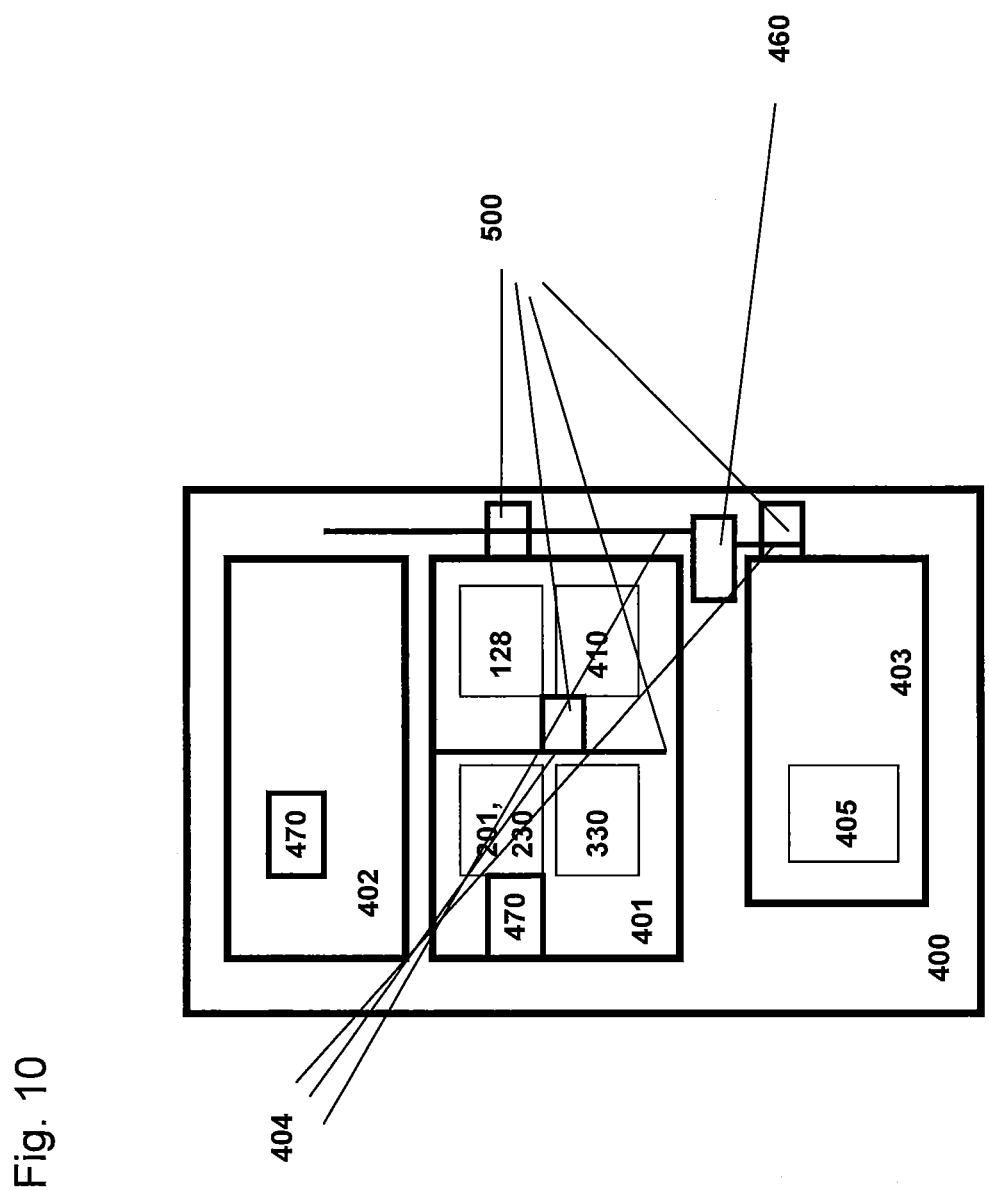
FIG. 10 shows a first schematic view of analytical system.

In one embodiment, an analytical system (440) for processing an analyte comprises, according to FIG. 10,
a) a first position comprising first receptacles (1001) in linear arrangement comprising liquid samples (1010), a processing plate (101) comprising receptacles (103) in nxm arrangement for holding a liquid sample (1011), a first pipetting device (700) comprising at least two pipetting units (702) in linear arrangement, wherein said pipetting units (702) are coupled to pipette tips (3, 4), and a tip rack (70) comprising pipette tips (3, 4) in an ax(nxm) arrangement;
b) a second position comprising a holder (201, 128) for said processing plate (101), a holder (470) for said tip rack (70) and a second pipetting device (35), said second pipetting device (35) comprising pipetting units (702) in an nxm arrangement for coupling to pipette tips (3, 4) (FIG. 10). The term "holder" as used herein relates to any arrangement capable of receiving a rack or a processing plate.

The advantages of the analytical system (440) of the present invention are as described herein for the method of the present invention.

The advantages of the analytical system (440) are as described herein.

In one embodiment, the position of said pipetting units (702) of the first pipetting device (700) are variable. Embodiments of said first pipetting device (700) are described herein.

In one embodiment, the tip rack (70) comprises pipette tips (3, 4) in an ax(nxm) arrangement. In one embodiment, a first type (4) and a second type (3) of pipette tips are comprised in the tip rack (70). In this embodiment, the first type of pipette tips (4) is arranged in an nxm arrangement, and the second type of pipette tips (3) is arranged in the nxm arrangement. In one embodiment, the first type of pipette tips (4) has a different volume than the second type of pipette tips (3). In one embodiment, the volume of the first type of pipette tips (4) is more than 500 ul, and the volume of the second type of pipette tips (3) is less than 500 ul. In this embodiment, a=2. However, embodiments of the invention with more than two types of pipette tips, and thus a>2 are also included in the present invention.

In one aspect, the analytical system (440) of the present invention comprises a control unit (1006) for allocating sample types and individual tests to individual positions of said processing plate (101). Preferably, said positions are separate cells (401, 402).

In one aspect of the invention, the system additionally comprises a transfer system (480) for transferring said process plate (101) and said rack (70) between first (402) and second (401) positions. Embodiments of said transfer system (480) are conveyor belts or, one or more handler.

Furthermore, said pipette units of said second pipetting device (35) are engaged to pipette tips (3, 4) which were used in the first position (402).

One embodiment of the system (440) described herein additionally comprises a third station (403) comprising a temperature-controlled incubator for incubating said analyte with reagents necessary to obtain a detectable signal. A further embodiment of third station (403) is a amplification station comprising a thermoblock. More optimal control of the allocation of samples and tests to the nxm arrangement is achieved with a first processor (1004) which is comprised in said first position (402) to which said control unit (1006) transfers instructions for allocating sample types and individual tests to specific positions in the nxm arrangement of vessels (103) of the process plate (101), and a second processor (1005) which is comprised in said second position (401) to which said control unit (1006) transfers instructions for allocating sample types and individual tests to specific positions in the nxm arrangement of vessels (103) of the process plate.

In one embodiment, the system additionally comprises a first processor located in said first position, and a second processor located in said second position.

In one embodiment, said first processor (1004) controls said first pipetting device (700) and said second processor (1005) controls said second pipetting device (35).

Temporary Store

The present disclosure also relates to an automated analyzer for isolating and/or analyzing an analyte which comprises a unit for transferring a liquid comprising a station for presenting at least one reagent cassette to a pipetting device. The analyzer additionally comprises a unit for analyzing an analyte. Furthermore, the analyzer also comprises a unit for temporary storage of at least one reagent cassette comprising reagents necessary to isolate and/or analyze said analyte.

The temporary storage makes it possible to store reagent cassettes while they are needed by the analyzer, and to remove them when they are not needed any longer.

In one embodiment, the unit for transferring a liquid additionally comprises at least one station for isolating an analyte. Embodiments for said station for isolating an analyte are described herein. The unit for transferring a liquid and the unit for temporary storage of at least one reagent cassette preferably overlap at least partially. In one embodiment, said station for presenting at least one reagent cassette to a pipetting device is located within said overlapping area. It is understood that said unit for transferring a liquid comprises at least one pipetting device. In one embodiment, the station for presenting at least one reagent cassette to a pipetting device is located outside the temporary store. In one embodiment, the overlapping area comprises an elevator plate.

In a further aspect of the present disclosure, the analyzer additionally comprises a unit for transferring a sample comprising an analyte from a first receptacle to a second receptacle. In one aspect of the present disclosure, the analyzer additionally comprises a closed reagent store.

In an embodiment of the analyzer, the unit for temporary storage comprises a cooling unit. Further embodiments of said temporary storage unit are disclosed herein.

Embodiments of said closed reagent store are described herein. The cooling unit of said closed reagent store is set to keep the inside temperature of the closed reagent store between a lower specified temperature and an upper specified temperature. Embodiments of said temperatures are disclosed herein.

The closed reagent store is particularly useful since it provides for long term storage of temperature sensitive reagents. Such reagents include, but are not limited to, reagents comprising enzymes, such as polymerases for amplifying nucleic acids, or enzymes for color reactions. The combination of a reagent store for long term storage of reagents and a temporary store according to the present disclosure is particularly advantageous in an analytical system. This reduces the time during which a reagent cassette and its contents are exposed to temperatures above the storage temperatures to a minimum. In such an analyzer and system, reagent cassettes with reagents can be loaded less frequently, thus increasing walk-away time for the operator. By transferring reagent cassettes from the reagent store to the temporary store, the reagent cassettes are presented to the pipetting device more quickly than if they had to be transferred directly from the reagent store. It allows for placing the reagent store in an area of the analyzer where space is readily available. The dimensions of the temporary storage unit can be reduced to the space necessary to store reagent cassettes required for a current run, thus making it possible to place it in close proximity of the unit for transferring liquids while minimizing the space occupied by the temporary storage unit. This setup is particularly advantageous for a quick and timely presentation of the reagent cassettes to the pipetting device when the respective reagents are needed.

The temporary store has further advantages. In one aspect, it comprises a closed cooling area with a cooling unit. In one aspect, said cooling is an active cooling unit. The cooling unit is set to keep the temperature below a threshold temperature. In one embodiment, the threshold temperature is 40° C., more preferably 35° C. or 30° C., most preferably 28° C. The cooling unit only has to operate to keep the temperature below such threshold. Thus, less energy is required than for the reagent store. On the other hand, the lifetime of the reagents is optimized because they only are kept in the temporary store as long as they are needed, and are then returned to the reagent store for long-term storage. The exposure to elevated temperature is thus minimized while quick and timely presentation of the reagent cassettes to the pipetting device is maintained.

Embodiments of the closed reagent store are described herein.

In one preferred aspect of the invention, the analyzer additionally comprises a handler system for bidirectional transport of said reagent cassette between said closed reagent store and said station for presenting a reagent cassette. Further preferred embodiments are described herein.

The present invention also relates to a method of presenting a reagent cassette comprising reagents for analyzing an analyte to a pipetting device within an automated analyzer, comprising the steps of:

transferring a reagent cassette stored in a closed reagent store with active cooling to a temporary storage unit;
holding said reagent cassette in said temporary storage unit until it is needed by the analyzer;

transferring said reagent cassette from said temporary storage unit to a station for presenting said reagent cassette to said pipetting device, wherein said station for presenting said at least one reagent cassette is located outside the temporary storage;

transferring said reagent cassette back to said temporary storage unit when pipetting of the reagent is finished.

Such a method is advantageous because the reagent cassettes comprising reagents are exposed to higher temperature areas within the analyzer only while they are needed, while they can be mobilized quickly when needed for pipetting.

In one aspect, steps b) to d) are repeated at least once. In one embodiment, said reagent cassette is transferred from said closed reagent store to said temporary storage unit with a handler system.

In one embodiment, said reagent cassette is transferred from said closed reagent store to a first position with a first handler, and from said first position to the temporary store with a second handler.

In one aspect, the reagent cassettes comprise a tag for storing information, wherein information of onboard time in the automated analyzer is stored on said tag.

In a preferred embodiment, the method herein described additionally comprises the step of transferring said reagent cassette to said closed reagent store for long term storage until the reagent comprised in said reagent cassette is required for a new test, if said reagent cassette is not empty, or transferring said reagent cassette to a consumable waste station. The reagent cassettes are additionally preferably manually loaded into a drawer of said closed reagent store, wherein said reagent cassette is automatically transferred within said closed reagent store.

In one embodiment, said reagent cassette in the temporary store is transferred to the station for presenting the reagent cassette to a pipetting device by an elevator.

Further preferred embodiments are as described herein.

Exemplary embodiments of the analyzer of the present invention and its components, in particular the temporary storage unit, are shown herein.

In one embodiment, the method herein described additionally comprises the step of transferring said reagent cassette to said closed reagent store for long term storage until the reagent comprised in said reagent cassette is required for a new test, if said reagent cassette is not empty, or transferring said reagent cassette to a consumable waste station. The reagent cassettes are additionally manually loaded into a drawer of said closed reagent store, wherein said reagent cassette is automatically transferred within said closed reagent store.

Further embodiments are as described herein.

Embodiments of the analyzer as disclosed herein and its components, in particular the temporary storage unit, are shown herein.

Figure 5:
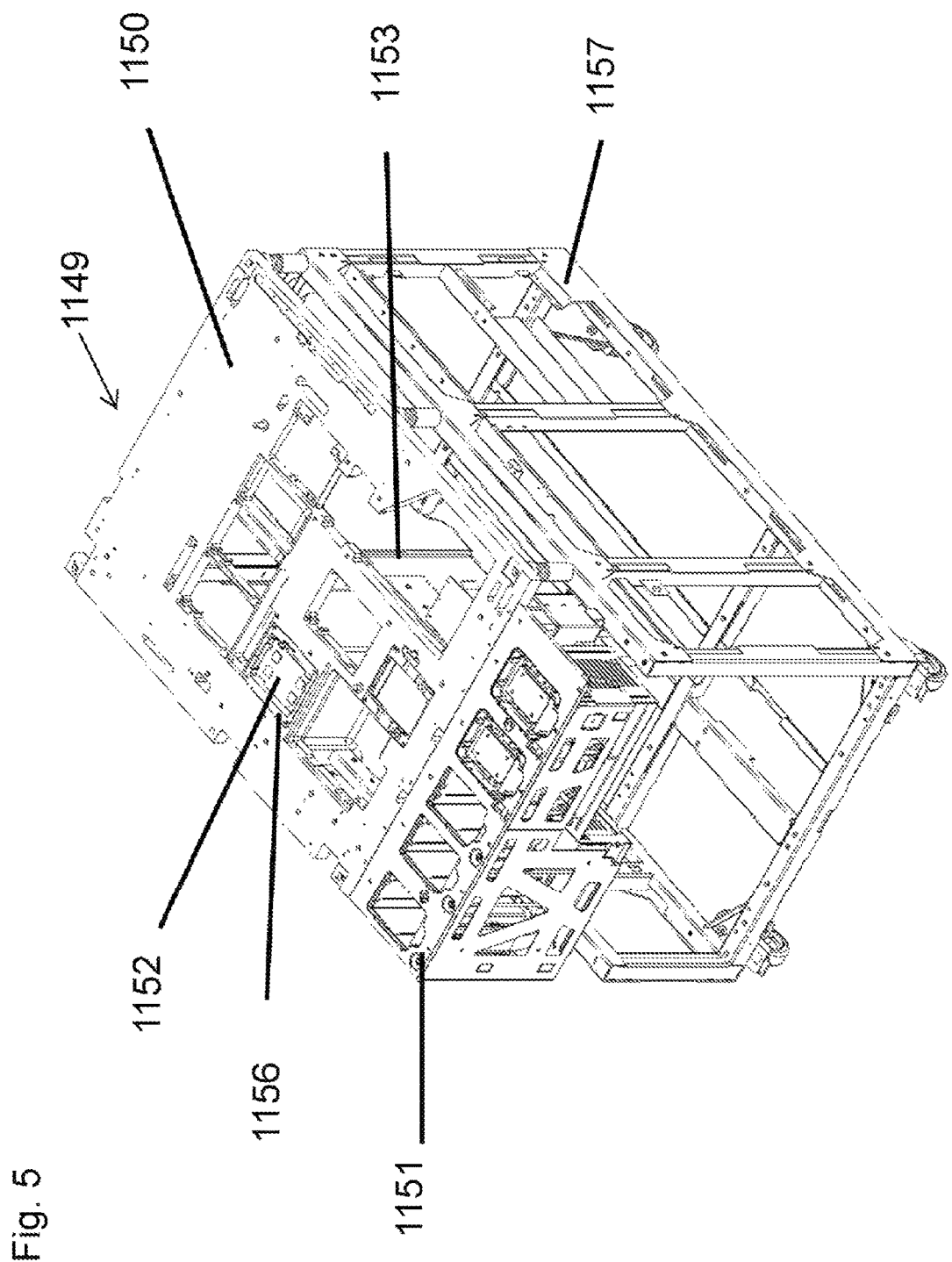
FIG. 5 shows a view of lower part of analyzer module with stackers and temporary store.
Figure 6:
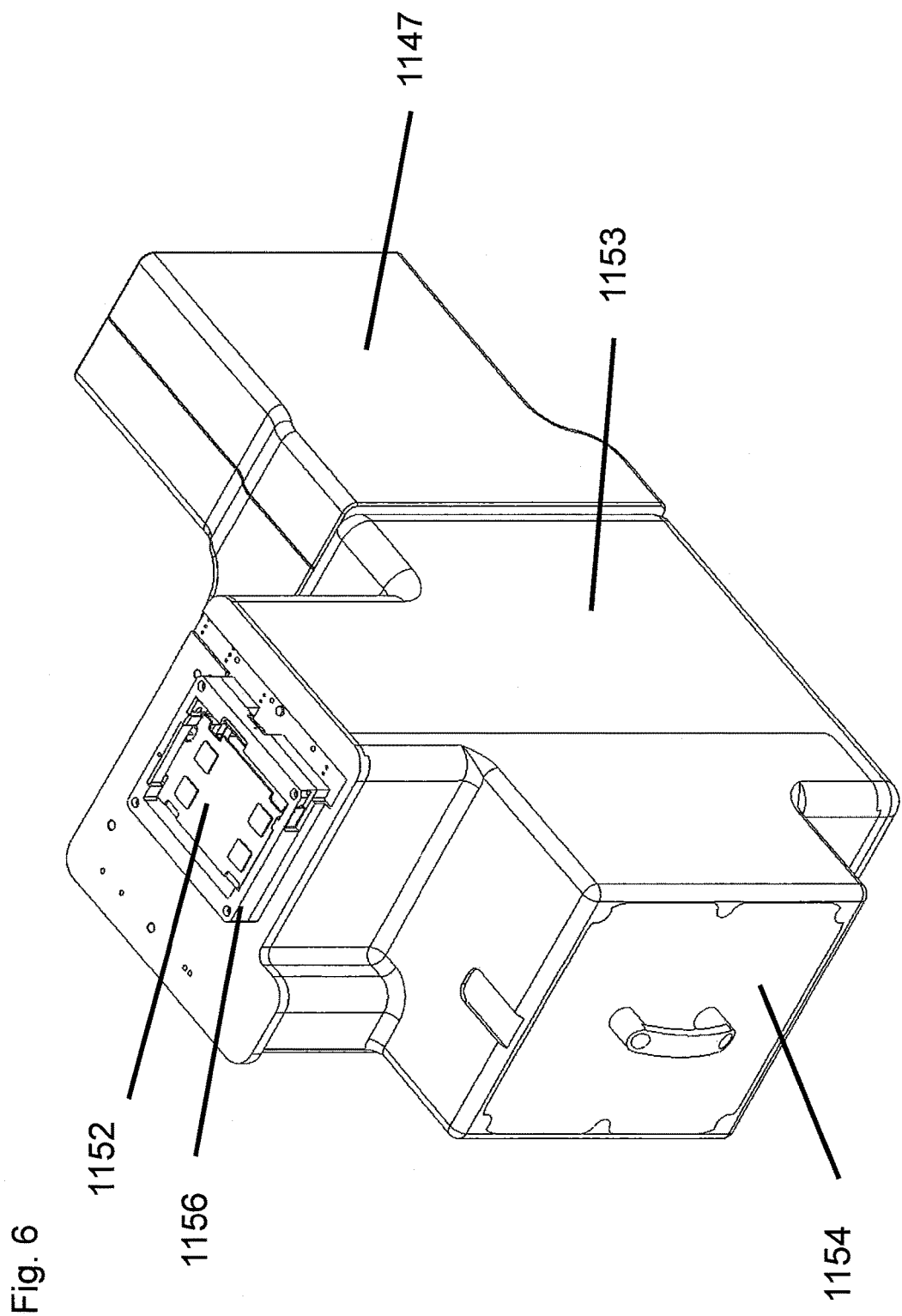
FIG. 6 shows a view of outside of temporary store.
Figure 7:
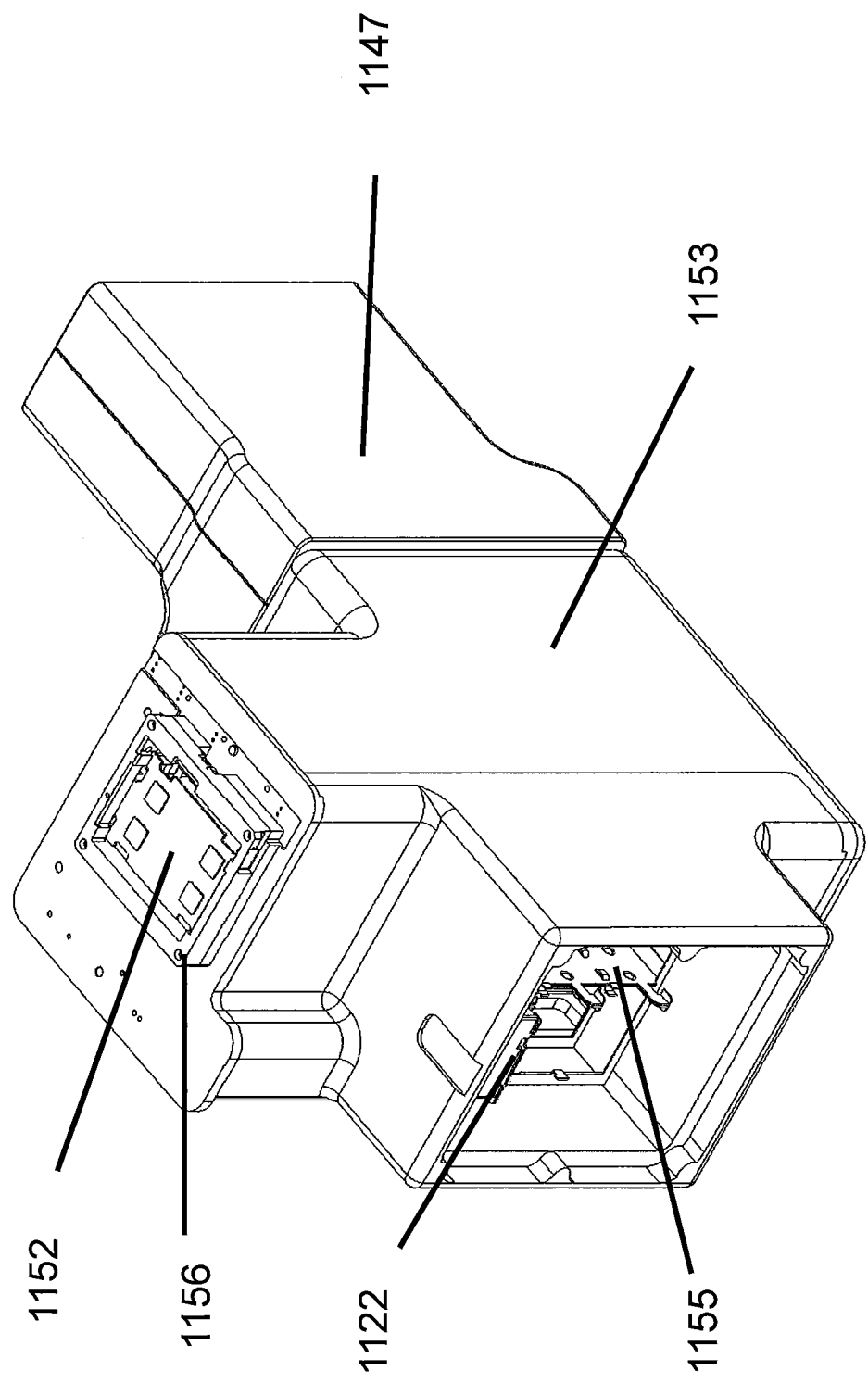
FIG. 7 shows a view of temporary store with open emergency door.
Figure 8:
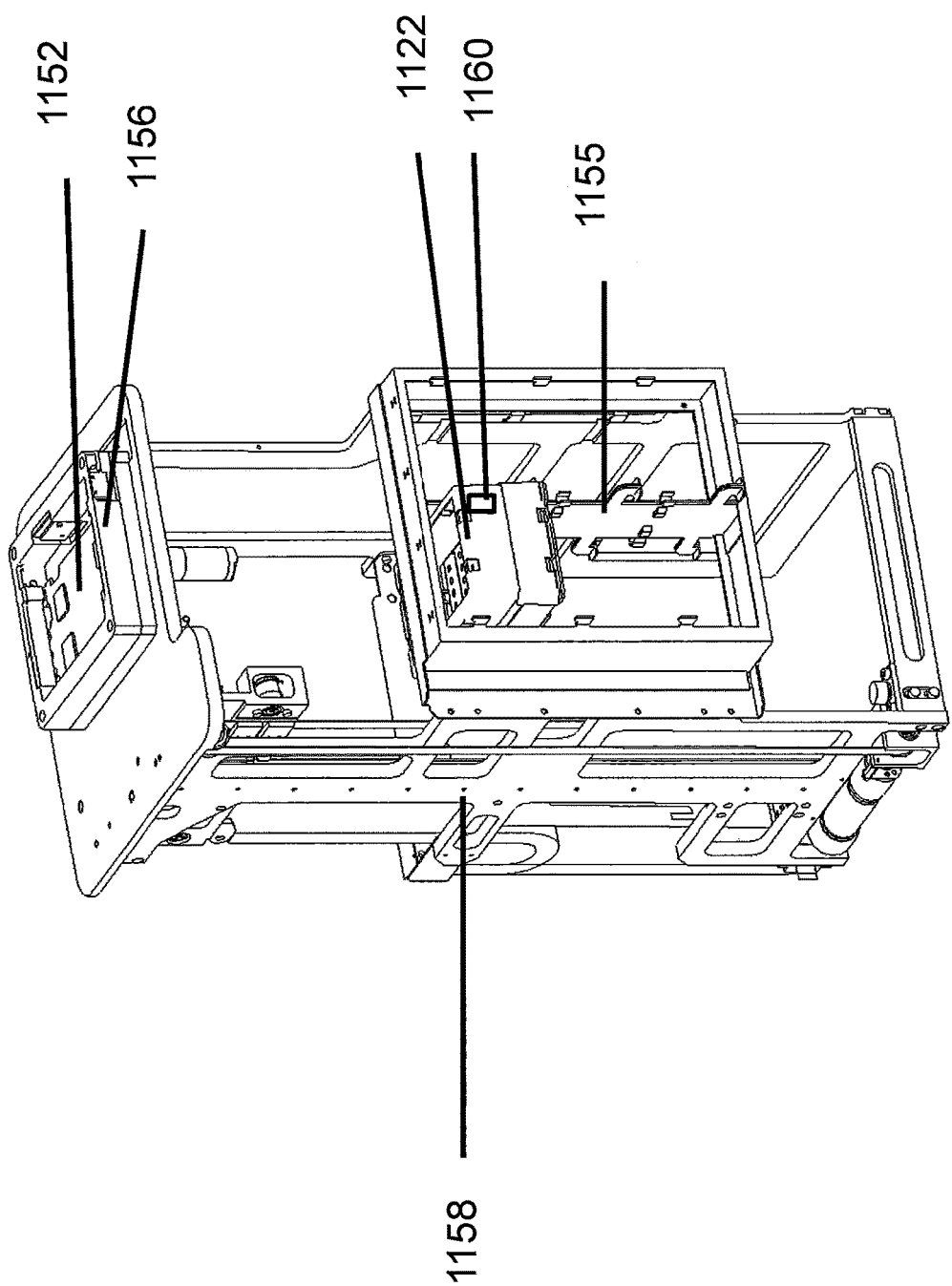
FIG. 8 shows a storage and retrieval system of temporary store.
Figure 9:
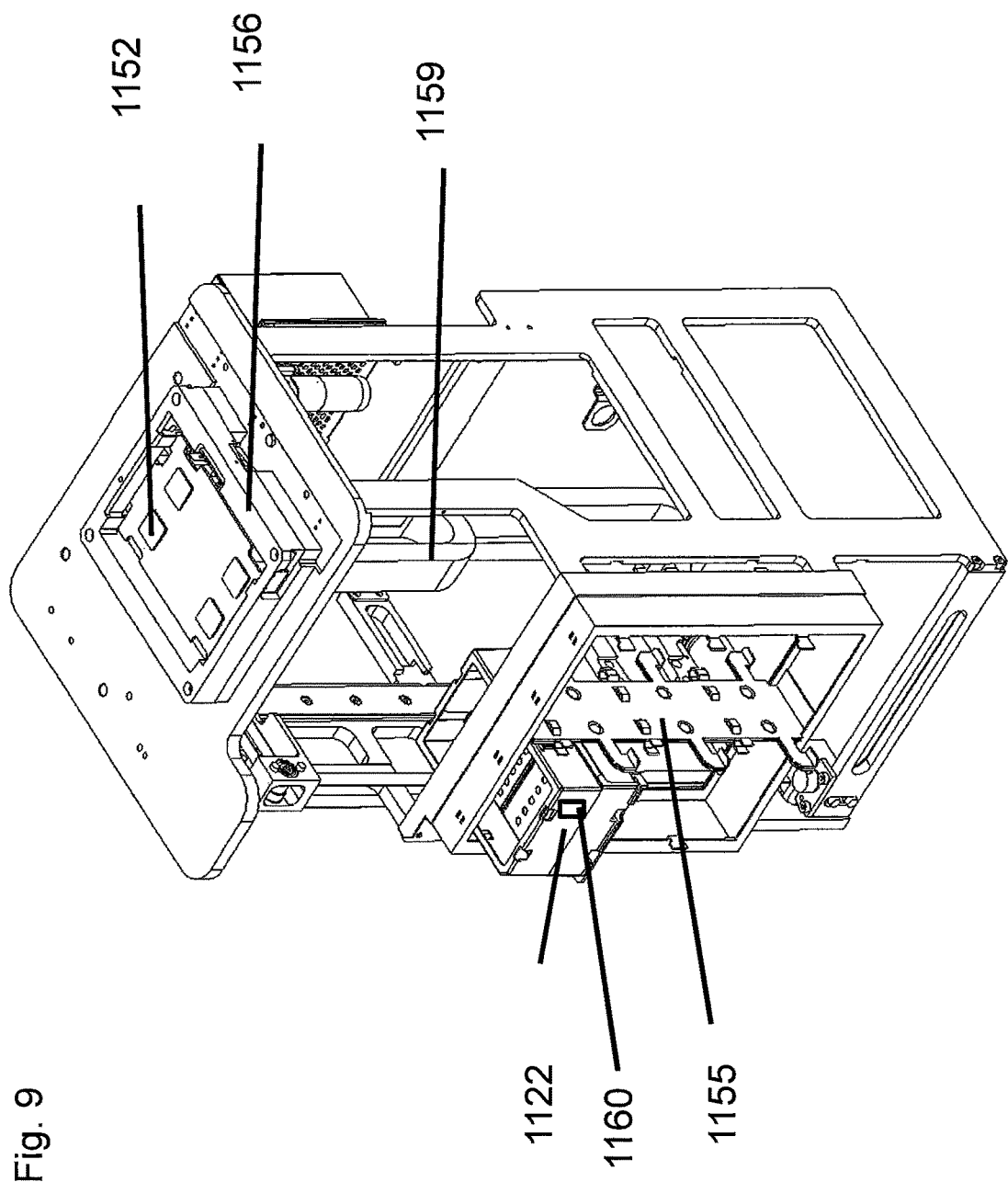
FIG. 9 shows a storage and retrieval system of temporary store with reagent cassette.

FIG. 5 shows a lower part (1149) of a module of an analyzer, which, in one embodiment is a processing module (402) (FIG. 10). The top of the lower part (1149) is a processing plate (1150). The lower part further comprises a frame (1157). A stacker (1151) is also shown. The processing plate (1150) comprises a station (1156) for presenting a reagent cassette (1122) (shown e.g. in FIG. 4) to a pipetting device and an elevator plate (1152) inside said station for presenting a reagent cassette (1122) to a pipetting device. The reagent cassette (1122) comprises a tag for storing information (1160). The elevator plate (1152) can be moved in Z direction. Also shown is the temporary store (1153). FIG. 6 shows a temporary store (1153), the station (1156) for presenting a reagent cassette to a pipetting device, and an emergency door (1154) for unloading the store and an air outlet (1147). FIG. 7 shows features as FIG. 6, except that the emergency door (1154) is removed and a holding unit (1155) for holding cassettes inside the temporary store (1153) and a cassette (1122) can be seen. The inside of the temporary store is shown in FIGS. 8 and 9. FIG. 8 shows a frame (1158), holding unit (1155), reagent cassette (1122) held in a holding unit, a station (1156) for presenting a reagent cassette (1122) and an elevator plate (1152). In particular, FIG. 9 also shows the elevator (1159).

Analytical Apparatus and Method for Isolating and Analyzing an Analyte

A method for isolating and analyzing an that may be present in a fluid sample is analyte is disclosed. Said method comprises the automated steps of f) transferring said fluid sample from a sample vessel to a processing vessel with a pipette tip;
g) combining together a solid support material and said fluid sample in a well of said processing vessel for a period of time and under conditions sufficient to permit said analyte to be immobilized on the solid support material;
h) isolating the solid support material from other material present in the fluid sample in a separation station;
i) and purifying the analyte in the separation station by separating the fluid sample from the solid support material and washing the materials one or more times with a wash buffer.

In one aspect, said pipette tip used in step a) is re-used after step a).

In the method herein described, step a) may further comprise a1) engaging pipette tips of a first type which are held in a rack in a first position with a first process head;
a2) transferring said fluid sample from a sample vessel to a processing vessel with pipette tips of a first type engaged to a first process head;
a3) placing said pipette tips in said rack and disengaging said pipette tips from said process head;
a4) transporting said rack comprising said pipette tips and said processing vessel to second positions;
a5) engaging said pipette tips of a first type which are held in said rack with a second process head in said second position.

In one embodiment, the processing vessel may comprise more than one receptacle. In one aspect, the processing vessel is a multiwell plate. The method preferably additionally comprises the step of j) reacting said purified analyte with reagents necessary to obtain a detectable signal.

Re-use of pipette tips leads to a reduction of disposable consumables used in the analytical method and to cost reductions. In one embodiment, the washing in step d) comprises aspirating and dispensing the washing buffer with a process head engaged to pipette tips.

In one embodiment, the reacting comprises generating a detectable signal. In one aspect, the method additionally comprises the step of detecting a detectable signal.

In one embodiment of the method herein described, the transporting of said rack comprising said pipette tips and said processing vessel to a second position occurs between a separate first cell of an analytical instrument and a separate second cell, which may be a processing cell, of said analytical system. In one aspect, the rack comprises independent chambers to accommodate pipette tips.

In one embodiment, the first type of pipette tips is re-used for the washing in step d).

In one embodiment, the rack additionally comprises a second type of pipette tips. Further, in one aspect the method as herein described comprises, between step d) and e), the analyte is eluted from the magnetic particles. One embodiment comprises the transfer of the analyte from said processing vessel, which is preferably a multiwell plate, to a reaction vessel, which is preferably a multiwell plate, with said second type of pipette tips.

The present disclosure describes an analytical system for isolating an analyte, said system comprising
 a) a first position comprising a first receptacle holding a liquid sample comprising an analyte, a second receptacle for holding a liquid sample, a rack holding pipette tips, and a first process head for transferring a liquid sample from the first receptacle to a second receptacle,
 b) a second position comprising a station for receiving said second receptacle, and a rack holding station for receiving said rack,
 c) a transfer system for transferring the second receptacle and the rack holding pipette tips between the first position and the second position.

In one embodiment, the positions are separate cells. The rack transferred by said transfer system comprises pipette tips which were used in the first position. In one embodiment, the first receptacle is a sample vessel and the second receptacle is a processing vessel. In one aspect, the processing vessel is a multiwell vessel. Embodiments of said stations are described herein.

In the analytical system herein described, the transport system preferably transfers the receptacle and the rack from the first position to the second separate position. In one aspect, the second separate position comprises a magnetic separation station. The analytical system additionally comprises, in another aspect, an amplification station.

The transport system of one embodiment of the system comprises a handler constructed and arranged to grip and transport said rack and said processing vessel from a first to a second location within the system. Handlers are known to the skilled person.

In one embodiment, the system is fully automated.

The present disclosure also relates to an automated analyzer for isolating and analyzing an analyte comprising a plurality of stations disposed within said analyzer. The plurality of stations comprises a sample dispensing station disposed in a first location. In one aspect, said sample dispensing station is constructed and arranged to dispense liquid sample comprising an analyte from a sample vessel to a processing vessel with pipette tips held in a rack. In one aspect, sample dispensing stations are stations comprising a sample vessel, a processing vessel and a liquid dispensing unit. Said liquid dispensing unit may be a process device.

The automated analyzer further comprises a separation station disposed in a second location. In one aspect, said separation station is constructed and arranged to receive said processing vessel holding said liquid sample and said rack holding pipette tips used in the sample dispensing station and to separate an analyte from other material present in the liquid sample. Another embodiment of a separation station is a separation station comprising movable magnets.

The automated analyzer further comprises a reaction station disposed in a third location, wherein said reaction station is constructed and arranged to analyze said analyte to obtain a detectable signal. Another embodiment of a reaction station is a station comprising an incubator. In one aspect, said incubator is a temperature-controlled incubator. In another aspect, said incubator is held at one constant temperature. Another embodiment of an incubator is a thermocycler block. In one aspect, a detector for detecting the detectable signal is integrally connected to the reaction station, or to the incubator. One embodiment of a detector comprises a nucleic acid quantification system for periodic measurement and quantification. In one aspect, the detector additionally comprises a nucleic acid detection system which detects the signal and ascertains the presence or absence of the nucleic acid in the reaction receptacle based upon whether or not a signal above a threshold level is detected.

Alternatively, the automated analyzer additionally comprises a detecting station. The automated analyzer further comprises a transport mechanism. Said transport mechanism comprises a handler for handling consumables. Said handler preferably transports a consumable between stations. In one embodiment, said transport mechanism is constructed and arranged to transport said sample vessel and said rack from said sample dispensing station to said separation station. Further embodiments of the automated analyzer of the present disclosure are individual or combined features disclosed herein.

In one embodiment, the analytical apparatus (400) of the present disclosure comprises at least one module (401) for processing an analyte, said processing comprising pipetting of a liquid. The processing module (401) comprises:
 a) a process head (35) for engaging with pipette tips (3, 4), said process head (35) comprising positioning elements (36) arranged in the lower surface (61) of said process head (35),
 b) a tip rack (60, 70) holding pipette tips (3, 4), wherein said tip rack (60, 70) comprises positioning elements (31, 32, 33, 34) capable of engaging mechanically with the positioning elements (36) on the process head (35).

In one embodiment of the analytical apparatus (400) herein described, said processing module (401) is a module for isolation and purification of an analyte. Therefore, the term "processing" as used herein is understood to relate to isolation and/or separation and/or capture and/or purification of an analyte. In one aspect, said apparatus (400) comprises a module for preparing samples for processing (402). In one aspect, said apparatus (400) comprises a module for amplification of said analyte (403). In one embodiment, said apparatus additionally comprises a module (404) for transferring amplification reagents from a storage receptacle to a receptacle comprising a purified analyte. Further embodiments of said apparatus are as herein and herein described.

The present disclosure also relates to an automated analyzer (400) for use in performing a nucleic acid based amplification reaction, said analyzer comprising a plurality of modules (401, 402, 403). One module is a processing module disposed at a first location within the analyzer constructed and arranged to separate a nucleic acid from other material in a sample. Said processing module comprises a separation device as herein described. The analyzer further comprises an amplification module disposed and arranged at a second location within the analyzer. The amplification module comprises a temperature-controlled incubator for incubating the contents of at least one receptacle, in one aspect of a multiwell plate comprising the separated nucleic acid and one or more amplification reagents for producing an amplification product indicative of the target nucleic acid in the sample.

The present disclosure also relates to an analytical system comprising a holding station and a multiwell plate set as described herein. In one embodiment, said multiwell plate set is fixed in said holding station. In one embodiment, the multiwell plate comprises a base with a rim which comprises recesses, wherein a positioning and fixing element, in one aspect a latch-clip (FIG. 47*a*) and *b*)), on said holding station contacts said recesses, wherein said contact exerts a downwards pressure on the base of the multiwell plate, thereby fixing the multiwell plate in the holding station. Further embodiments of the analytical system comprise individual or combined features described herein.

The present disclosure also relates to an analytical instrument comprising:
- a processing module for isolating and purifying an analyte comprising a holding station (470) for holding a rack comprising pipette tips, said rack comprising at least one recess located on one side wall of the rack, and at least one recess located on an opposite second side wall of said rack, wherein said holding station comprises a fixing element, in one aspect a latch-clip and wherein said fixing element, or a latch-clip interacts with said recess by exerting a force against the bottom of said recess; and
- a module (403) for analyzing said purified analyte by reacting said analyte with reagents necessary to obtain a detectable signal.

The analytical instrument, in one aspect, additionally comprises a liquid handling module (404, 500). Further embodiments of the analytical instrument are described herein, either separately or as combinations of embodiments. In one aspect, the analytical instrument according to the present disclosure preferably additionally comprises a sealing station (410). The sealing station (410) is located in the process module (401).

The term "module" and "cell" are used interchangeably herein.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed:

1. A method of providing reagent cassettes to an analytical system comprising:
   (i) a closed reagent store and (ii) a temporary store, each of (i) and (ii) comprising (x) a loading interface adapted to receive one or more reagent cassettes, (y) an internal storage and retrieval system including an elevator having a Y-handler and an X-axis, and (z) an identification unit configured to read and write information to and from an RFID tag positioned on said reagent cassette and thereby identify said reagent cassette, wherein said information comprises an on-board time stamp; and
   (iii) a transport system comprising an additional handler, wherein said transport system is configured for bidirectional transport of said reagent cassette between one or more of said reagent store, said temporary store, and one or more stations of said analytical system;
   wherein said analytical system is operably connected to a control unit configured to determine a cumulated on-board time of a reagent cassette in said temporary store, and one or more of said stations of said analytical system and transfer instructions to one or more of said reagent store and said temporary store regarding reagent cassette requirements for said analytical system;
   the method comprising the steps of:
   a) loading a plurality of reagent cassettes into said loading interface;
   b) identifying said reagent cassettes using said identification unit;
   c) positioning, automatically, said reagent cassettes in said reagent store by said elevator;
   d) transferring said instructions from said control unit to said reagent store;
   e) removing a reagent cassette from said reagent store using said additional handler and triggering the identification unit to write to said RFID an on-board time stamp to said RFID which corresponds to the time the reagent cassette is removed from said reagent store;
   f) transporting said reagent cassette with said additional handler to a station of said analytical system;
   g) comparing said on-board time stamp to an actual time to calculate a cumulated on-board time; and
   h) returning said reagent cassette to one of said reagent store and said temporary store if the cumulated on-board time is less than a preset value and transferring said reagent cassette to a waste station when the cumulated on-board time exceeds said preset value,
   wherein steps b) to i) are automated.

2. The method according to claim 1, wherein said reagent store is cooled by an active cooling unit.

3. The method of claim 1, wherein step f) comprises transporting said reagent cassette to a station comprising a pipetting device.

4. The method of claim 1, wherein step h) comprises returning said reagent cassette to said reagent store for long term storage.

5. The method of claim 1, wherein said preset value is dependent on a temperature in one or more of said temporary store and said station of said analytical system.

* * * * *